United States Patent
Palmer (10) Patent No.: US 7,925,350 B1
(45) Date of Patent: Apr. 12, 2011

(54) SYSTEMS AND METHODS FOR DETECTING AN ERROR ASSOCIATED WITH AN IMPLANTABLE DEVICE

(75) Inventor: Logan P. Palmer, Santa Monica, CA (US)

(73) Assignee: Advanced Bionics, LLC, Valencia, CA (US)

( * ) Notice: Subject to any disclaimer, the term of this patent is extended or adjusted under 35 U.S.C. 154(b) by 0 days.

(21) Appl. No.: 12/879,174

(22) Filed: Sep. 10, 2010

Related U.S. Application Data (62) Division of application No. 11/580,498, filed on Oct. 13, 2006, now Pat. No. 7,818,061.

(51) Int. Cl.
*A61N 1/08* (2006.01)

(52) U.S. Cl. ............... 607/32; 607/27; 607/55; 607/56; 607/57; 607/59

(58) Field of Classification Search ............ 607/27, 607/31, 32, 55–57, 59, 60
See application file for complete search history.

(56) References Cited

U.S. PATENT DOCUMENTS

| | | | |
|---|---|---|---|
| 3,920,025 A | 11/1975 | Stasz et al. | |
| 4,532,930 A | 8/1985 | Crosby et al. | |
| 5,522,865 A | 6/1996 | Schulman et al. | |
| 5,531,774 A | 7/1996 | Schulman et al. | |
| 5,603,726 A | 2/1997 | Schulman et al. | |
| 5,876,425 A | 3/1999 | Gord et al. | |
| 6,195,585 B1 | 2/2001 | Karunasiri et al. | |
| 6,219,580 B1 | 4/2001 | Faltys et al. | |
| 6,745,077 B1 | 6/2004 | Griffith et al. | |
| 2003/0229383 A1 | 12/2003 | Whitehurst et al. | |

OTHER PUBLICATIONS

Non-Final Office Action received in U.S. Appl. No. 11/580,498 dated Jan. 22, 2009.
Final Office Action received in U.S. Appl. No. 11/580,498 dated Jul. 10, 2009.
Non-Final Office Action received in U.S. Appl. No. 11/580,498 dated Jan. 20, 2010.

*Primary Examiner* — Niketa I Patel
*Assistant Examiner* — Hiba El-Kaissi
(74) *Attorney, Agent, or Firm* — AdvantEdge Law Group, LLC (57) ABSTRACT

Methods of detecting an error associated with an implantable device include powering up the implantable device with an external device, disabling a back-telemetry transmitter within the implanted device after the implanted device is powered up, detecting an error with the implanted device, generating a fault signal corresponding to the error with the implanted device, turning on the back-telemetry transmitter after the fault signal has been generated, and transmitting the fault signal to the external device with the back-telemetry transmitter.

15 Claims, 7 Drawing Sheets

SYSTEMS AND METHODS FOR DETECTING AN ERROR ASSOCIATED WITH AN IMPLANTABLE DEVICE

RELATED APPLICATIONS

The present application is a divisional application of U.S. patent application Ser. No. 11/580,498, filed Oct. 13, 2006, which is incorporated herein by reference in its entirety.

BACKGROUND

It is often desirable for electronic devices to transmit data, transfer power, or otherwise communicate one with another. Reliable communication is especially important in medical devices, where miscommunication may result in device malfunction and harm to a patient. For example, many implantable medical devices, such as implantable stimulators, are configured to transmit status updates to and receive operational instructions and power from one or more external devices. Without accurate communication, these implantable medical devices could cease to function properly.

An exemplary implantable medical device is an implantable cochlear stimulator (ICS), which may be used to treat sensorineural hearing loss. An ICS seeks to bypass the hair cells in the cochlea, which are essential to hearing but which may not be functioning properly, by presenting electrical stimulation directly to the auditory nerve fibers. The stimulation leads to the perception of sound in the brain and at least partial restoration of hearing function.

Many implantable medical devices are intended to remain permanently in the body of a patient once they are implanted. For this reason, one or more external devices may be configured to communicate with and support an implantable medical device by transmitting various control signals (e.g., stimulation parameters) to the implantable medical device and/or provide power to the implantable medical device. For example, a behind-the-ear (BTE) signal processor may be positioned behind the ear and used to support the ICS by transmitting various stimulation parameters to the ICS and/or providing power to the ICS.

An external device may also be configured to periodically receive status signals from an implantable medical device to ensure that the implantable medical device is functioning properly. To this end, implantable medical devices often include a back-telemetry transmitter configured to transmit one or more status signals to an external device via, e.g., a wireless telemetry link.

However, back-telemetry transmitters often consume a relatively large amount of power. Hence, the current drain on the implantable medical device caused by enabling the back-telemetry transmitter can significantly lower the power supply voltage(s) in the implantable medical device.

In cases where the implantable medical device includes an ICS, the current drain caused by back-telemetry transmitters is often perceptible to the user due to reduced stimulation compliance voltages. To alleviate the reduced compliance voltage levels, the back-telemetry transmitter may be enabled or left "on" at all times. However, this requires additional power to be supplied to the ICS continuously, which may lead to reduced battery life in the BTE signal processor.

Alternatively, the BTE signal processor may temporarily increase the power supplied to the ICS prior to turning on the back-telemetry transmitter in order to alleviate the reduced stimulation compliance voltages. However, such an approach adds undesirable cost and complexity to the system power management hardware and software, induces perceptible noise into the processor audio circuits due to rapidly switching loads on the processor's power supply, and, in some cases, can still cause perceptible fluctuations in the compliance voltage.

SUMMARY

Systems for detecting an error associated with an implantable device include a back-telemetry transmitter within the implantable device configured to transmit one or more signals to an external device having a receiver configured to receive the one or more signals. The implantable device includes circuitry configured to detect an error associated with the implantable device, generate a fault signal corresponding to the error, and turn on the back-telemetry transmitter to transmit the fault signal to the external device.

Methods of detecting an error associated with an implantable device include powering up the implantable device with an external device, disabling a back-telemetry transmitter within the implanted device after the implanted device is powered up, detecting an error with the implanted device, generating a fault signal corresponding to the error with the implanted device, turning on the back-telemetry transmitter after the fault signal has been generated, and transmitting the fault signal to the external device with the back-telemetry transmitter.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Systems and methods for detecting an error associated with an implantable device are described herein. The implantable device may include any device that is implanted within a patient to perform any function. Exemplary, but not exclusive, implantable devices include stimulators, pacemakers, defibrillators, implantable drug delivery systems, sensors, and other types of implantable medical devices. However, for illustrative purposes only, an implantable stimulator will be used to illustrate the exemplary embodiments described herein.

As will be described in more detail below, an exemplary system includes an implantable device and an external device. The external device includes a forward-telemetry transmitter configured transmit one or more signals to the implantable device. Likewise, the implantable device includes a back-telemetry transmitter configured to transmit one or more signals to the external device via a back-telemetry link. The implantable device includes a number of components configured to allow the implantable device to automatically enable the back-telemetry transmitter and send one or more fault signals to the external device when an error associated with the implantable device is detected.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
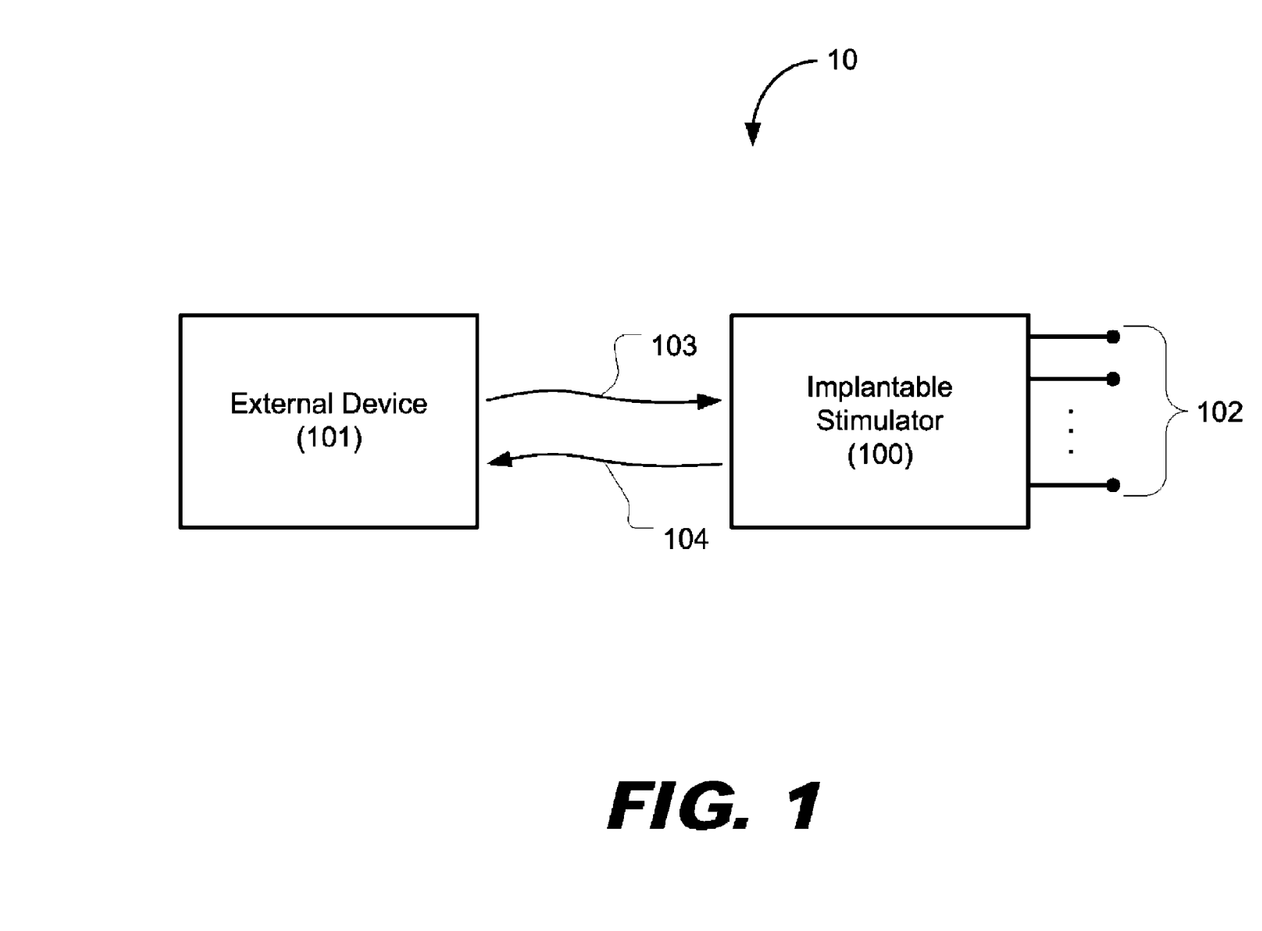
FIG. 1 illustrates an exemplary stimulation system according to principles described herein.

FIG. 1 illustrates an exemplary stimulation system 10. As shown in FIG. 1, the system 10 includes an implantable stimulator 100 configured to communicate with an external device 101 via one or more communication links 103, 104. It will be recognized that the stimulator 100 of FIG. 1 is merely illustrative of the many different types of implantable devices that may be used in connection with the systems and methods described herein.

As shown in FIG. 1, the stimulator 100 may include a number of electrodes 102 that may be configured to apply an electrical stimulation to one or more stimulation sites within a patient. The function of the electrodes 102 will be described in more detail below. The stimulator 100 may additionally or alternatively include one or more catheters (not shown) through which one or more drugs may be infused at one or more stimulation sites.

The external device 101 may include any device configured to communicate with and/or control the implantable stimulator 100. For example, the external device 101 may include, but is not limited to, a BTE signal processor, a programming device, or an external power charger. In some examples, the external device 101 may be configured to transmit control data, stimulation parameters, power signals, and/or other signals to the stimulator 100 via a first communication link 103, also referred to as a forward-telemetry link. Likewise, the implantable stimulator 100 may be configured to transmit status signals and/or other signals to the external device 101 via a second communication link 104, also referred to as a back-telemetry link. In some alternative examples, the first and second communication links 103, 104 may be combined into a single bi-directional communication link.

Before discussing the present systems and methods for monitoring the status of an implantable device, it is helpful to understand the components of a number of exemplary implantable stimulators with which the present systems and methods may be employed.

Figure 2:
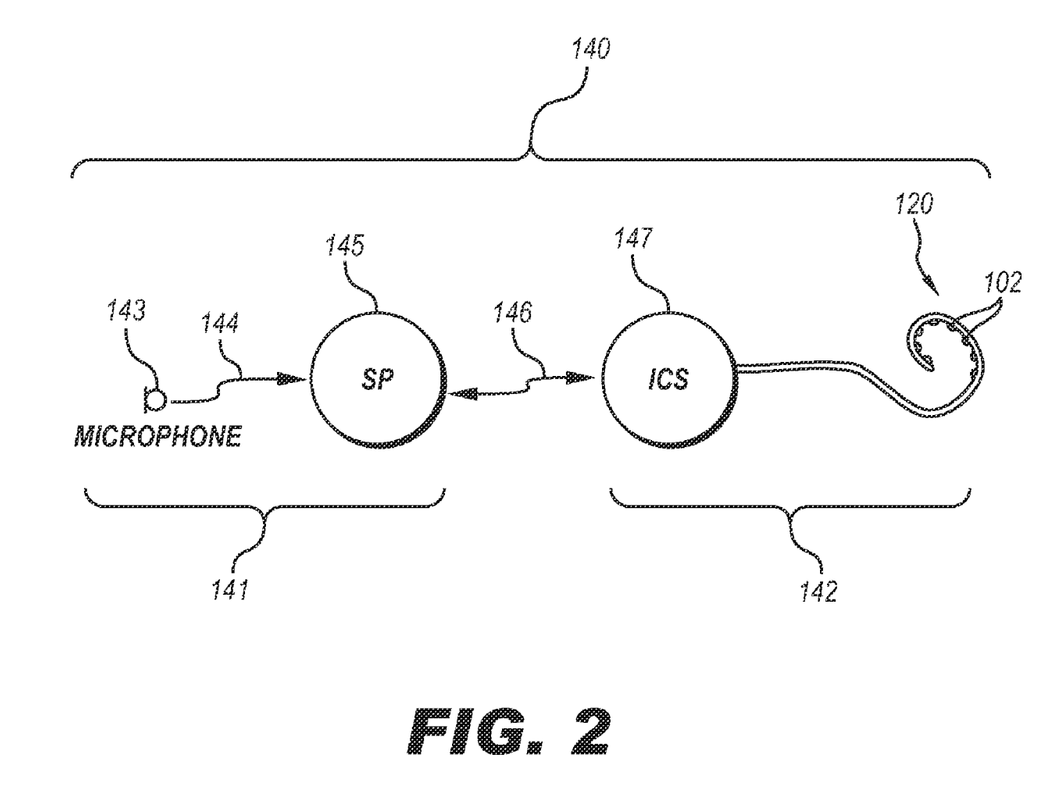
FIG. 2 shows an exemplary cochlear implant system according to principles described herein.

FIG. 2 shows an exemplary cochlear implant system 140 that may be used as an implantable stimulator in accordance with the present systems and methods. Exemplary cochlear implant systems suitable for use as described herein include, but are not limited to, those disclosed in U.S. Pat. Nos. 6,219,580; 6,272,382; and 6,308,101, all of which are incorporated herein by reference in their respective entireties. The cochlear implant system 140 includes a speech processor portion 141 and a cochlear stimulation portion 142. The speech processor portion 141 may include a speech processor (SP) 145 (e.g., a BTE signal processor), a microphone 143, and/or additional circuitry as best serves a particular application. The cochlear stimulation portion 142 may include an implantable cochlear stimulator (ICS) 147, a number of electrodes 102 disposed on a lead 120, and/or additional circuitry as best serves a particular application. The components within the speech processor portion 141 and the cochlear stimulation portion 142 will be described in more detail below.

The microphone 143 of FIG. 2 is configured to sense acoustic signals and convert such sensed signals to corresponding electrical signals. The electrical signals are sent to the SP 145 via a communication link 144. Alternatively, the microphone 143 may be connected directly to, or integrated with, the SP 145. The SP 145 processes these converted acoustic signals in accordance with a selected speech processing strategy to generate appropriate stimulation parameters for controlling the ICS 147. These parameters may specify or define the polarity, magnitude, location (i.e., which electrode pair or electrode group receive the stimulation current), and timing (i.e., when the stimulation current is to be applied to a particular electrode pair) of the stimulation current that is generated by the ICS 147.

The lead 120 of FIG. 2 is configured to be inserted within a duct of the cochlea. As shown in FIG. 2, the lead 120 includes a multiplicity of electrodes 102, e.g., sixteen electrodes, spaced along its length. The lead 120 may be substantially as shown and described in U.S. Pat. No. 4,819,647 or 6,129,753, each of which is incorporated herein by reference in its respective entirety. Electronic circuitry within the ICS 147 is configured to generate stimulation current via selected pairs or groups of the individual electrodes 102 in accordance with a specified stimulation pattern defined by the SP 145.

The ICS 147 and the SP 145 may be electronically connected via a suitable data or communication link 146. It will be understood that the data communication link 146 may include a bi-directional communication link and/or one or more dedicated uni-directional communication links, such as the forward and back-telemetry links 103, 104 shown in FIG. 1.

In some examples, the SP 145 and the microphone 143 are located comprise an external portion of the cochlear implant system 140 and the ICS 147 and the electrode lead 120 comprise an implantable portion of the system 140 that is implanted within a patient's body. In alternative embodiments, one or more portions of the SP 145 are included within the implantable portion of the cochlear implant system 140.

The external and implantable portions of the cochlear implant system 140 may each include one or more coils configured to transmit and receive power and/or control signals via the communication link 146. For example, the external portion of the cochlear implant system 140 may include an external coil (not shown) and the implantable portion of the cochlear implant system 140 may include an implantable coil (not shown). The external coil and the implantable coil may be inductively coupled to each other, thereby allowing data to be transmitted therebetween. The data may include, for example, the magnitude and polarity of a sensed acoustic signal. The external coil may also transmit power from the external portion to the implantable portion of the cochlear implant system 140. It will be noted that, in some embodiments, both the SP 145 and the ICS 147 may be implanted within the patient, either in the same housing or in separate housings. If the SP 145 and the ICS 147 are in the same housing, the communication link 146 may be realized with a direct wire connection within such housing. If the SP 145 and the ICS 147 are in separate housings, the communication link 146 may include one or more inductive links, for example.

Figures 3A, 3B:
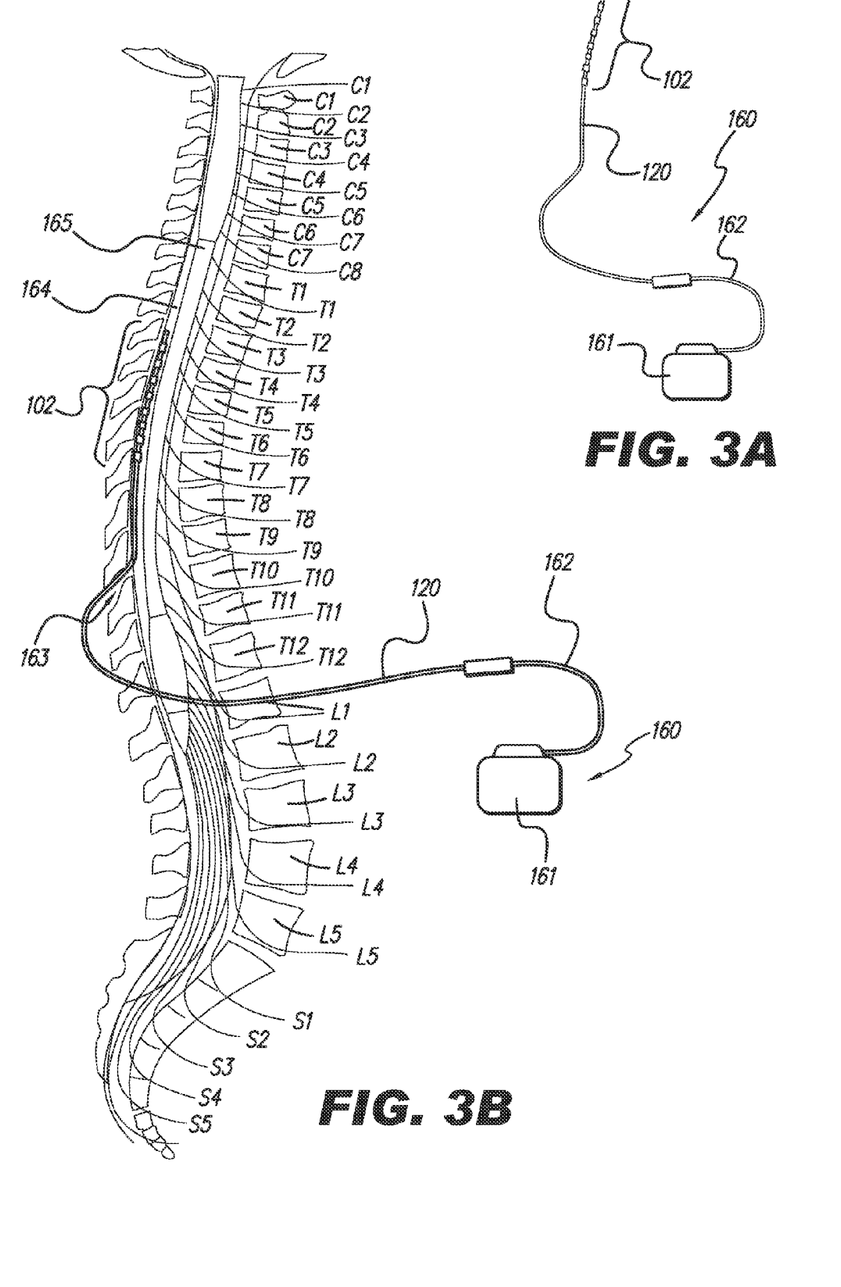
FIGS. 3A and 3B illustrate an exemplary spinal cord stimulator system according to principles described herein.

The implantable stimulator 100 of FIG. 1 may alternatively include a spinal cord stimulator (SCS). FIGS. 3A and 3B illustrate an exemplary spinal cord stimulator system 160. The SCS 160 may be used to treat a number of different medical conditions such as, but not limited to, chronic pain.

As shown in FIG. 3A, the SCS 160 may include an implantable pulse generator (IPG) 161, a lead extension 162, and a lead 120 having an array of electrodes 102 disposed thereon. The electrodes 102 may be arranged, as shown in FIG. 3A, in an in-line array near the distal end of the lead 120. Other electrode array configurations may additionally or alternatively be used. The lead extension 162 need not always be used with the SCS 160, but may be used depending on the physical distance between the IPG 161 and the stimulation site within the patient. The IPG 161 is configured to generate stimulation current pulses that are applied to a stimulation site via one or more of the electrodes 102. Exemplary spinal cord stimulators suitable for use as described herein include, but are not limited to, those disclosed in U.S. Pat. Nos. 5,501,703; 6,487,446; and 6,516,227, all of which are incorporated herein by reference in their respective entireties.

FIG. 3B shows that the array of electrodes 102 of the SCS 160 may be implanted in the epidural space 164 of a patient in close proximity to the spinal cord 165. Because of the lack of space near the lead exit point 163 where the electrode lead 120 exits the spinal column, the IPG 161 is generally implanted in the abdomen or above the buttocks. However, it will be recognized that the IPG 161 may be implanted in any suitable implantation site. The lead extension 162 facilitates implanting the IPG 161 at a location that is relatively distant from the lead exit point 163.

The cochlear implant system 140 and the SCS 160 are merely illustrative of many types of stimulators that may be implanted within a patient and configured to apply one or more stimuli at a stimulation site. For example, the implantable stimulator 100 may additionally or alternatively include a deep brain stimulator, an implantable microstimulator, or any other type of stimulator configured to perform neural response imaging. Exemplary deep brain stimulators suitable for use as described herein include, but are not limited to, those disclosed in U.S. Pat. Nos. 5,938,688; 6,016,449; and 6,539,263. Exemplary implantable microstimulators suitable for use as described herein include, but are not limited to, those disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

Figure 4:
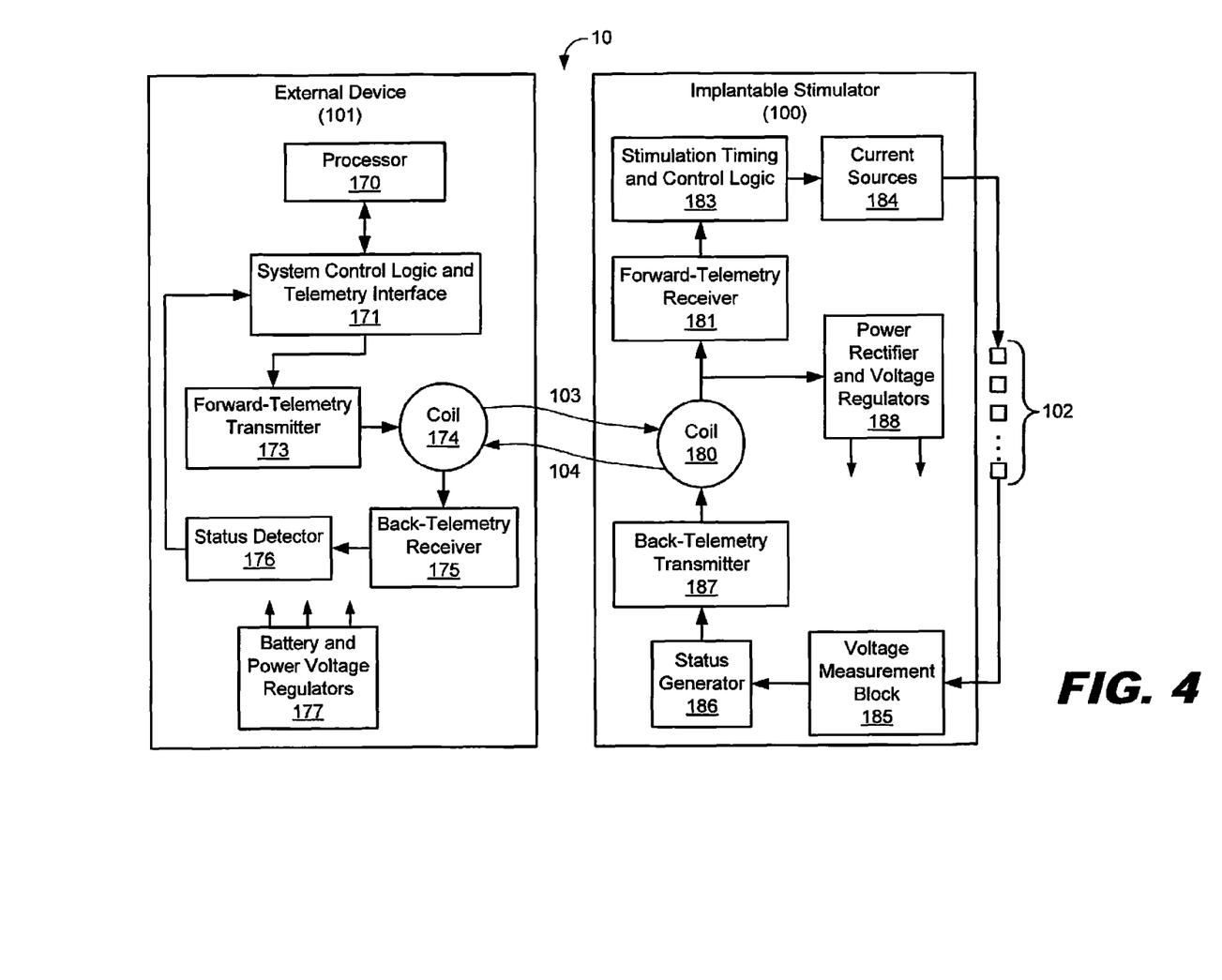
FIG. 4 is a more detailed functional block diagram of the stimulation system shown in FIG. 1 according to principles described herein.

FIG. 4 is a more detailed functional block diagram of the stimulation system 10 shown in FIG. 1. It will be recognized that the stimulation system 10 may be configured to perform additional or alternative functions as best serves a particular application. Moreover, it will be recognized that each of the functional blocks shown in FIG. 4 may include any combination of hardware, software, and/or firmware as best serves a particular application.

As shown in FIG. 4, the external device 101 may include a processor 170 configured to process data that is input into the system. For example, in the case of a cochlear implant system, the processor 170 may be configured to receive and process audio signals. Alternatively, the data may be input manually by a clinician, derived from data transmitted from the implantable stimulator 100, or otherwise provided to the processor 170.

The external device 101 may also include system control logic and a telemetry interface 171. The control logic and telemetry interface 171 may be configured to configure the processed data for transmission via the forward-telemetry link 103 and/or perform other functions within the external device 101.

A forward-telemetry transmitter 173 may be configured to transmit data and/or power signals to the implantable stimulator 100 via the forward-telemetry link 103. In some examples, the external device 101 and stimulator 100 both include one or more coils 174, 180 configured to facilitate wireless communication therebetween. Additionally or alternatively, the external device 101 and stimulator 100 may include one or more alternative means of communication.

The external device 101 may also include a back-telemetry receiver 175 and status detector 176. The back-telemetry receiver 175 may be configured to receive one or more types of data signals from the implantable stimulator 100 via the back-telemetry link 104. For example, as will be described in more detail below, the back-telemetry receiver 175 may receive one or more signals indicating the status of the implantable stimulator 100. The status detector 176 may include one or more components configured to detect the status of the implantable stimulator 100 by processing the received status signals.

The external device 101 may also include one or more battery and power voltage regulators 177. In some examples, the regulators 177 are configured to provide power to one or more of the components within the external device 101. In some examples, the regulators 177 are additionally configured to provide power to the implantable stimulator 100 via the forward-telemetry link 103.

As shown in FIG. 4, the implantable stimulator 100 may include one or more components configured to receive data and/or power signals from the external device 101. In particular, the stimulator 100 may include a forward-telemetry receiver 181 configured to demodulate the digital data stream transmitted by the external device 101. Stimulation timing and control logic 183 may be configured to use the demodulated data signals to drive one or more current sources 184 and cause the current sources 184 to generate stimulation current in accordance with one or more stimulation parameters included within the demodulated data. The stimulation current may then be applied to one or more stimulation sites within the patient via one or more electrodes 102.

In some examples, the stimulator 100 may include a voltage measurement block 185 configured to measure voltages at the electrodes 102 to assess such factors as electrode impedance and evoked neural potentials. The voltage measurement block 185 may additionally or alternatively be configured to measure internal supply voltages of the stimulator 100 for diagnostic and other purposes.

As shown in FIG. 4, the stimulator 100 may also include a status generator 186 configured to generate one or more status signals configured to indicate the status or state of the stimulator 100. For example, the status signals may include, but are not limited to, data indicative of one or more power or voltage levels within the stimulator 100, functionality indicators, errors, and/or any other information regarding the state of the implantable stimulator 100.

In some examples, a back-telemetry transmitter 187 may also be included within the implantable stimulator 100. The back-telemetry transmitter 187 is configured to transmit data to the external device 101 and may be used to transmit one or more of the status signals back to the external device 101. The back-telemetry transmitter 187 will be described in more detail below.

The stimulator 100 may also include one or more power rectifiers and/or voltage regulators 188. In some examples, these components may be configured to extract DC power from one or more power signals received by the coil 180 and supply the DC power to various components within the stimulator 100. The voltage regulators 188 may additionally regulate various power supply voltages within the stimulator 100, including, but not limited to, the compliance voltages used by the current sources 184 and the power used by the back-telemetry transmitter 187.

Figure 5:
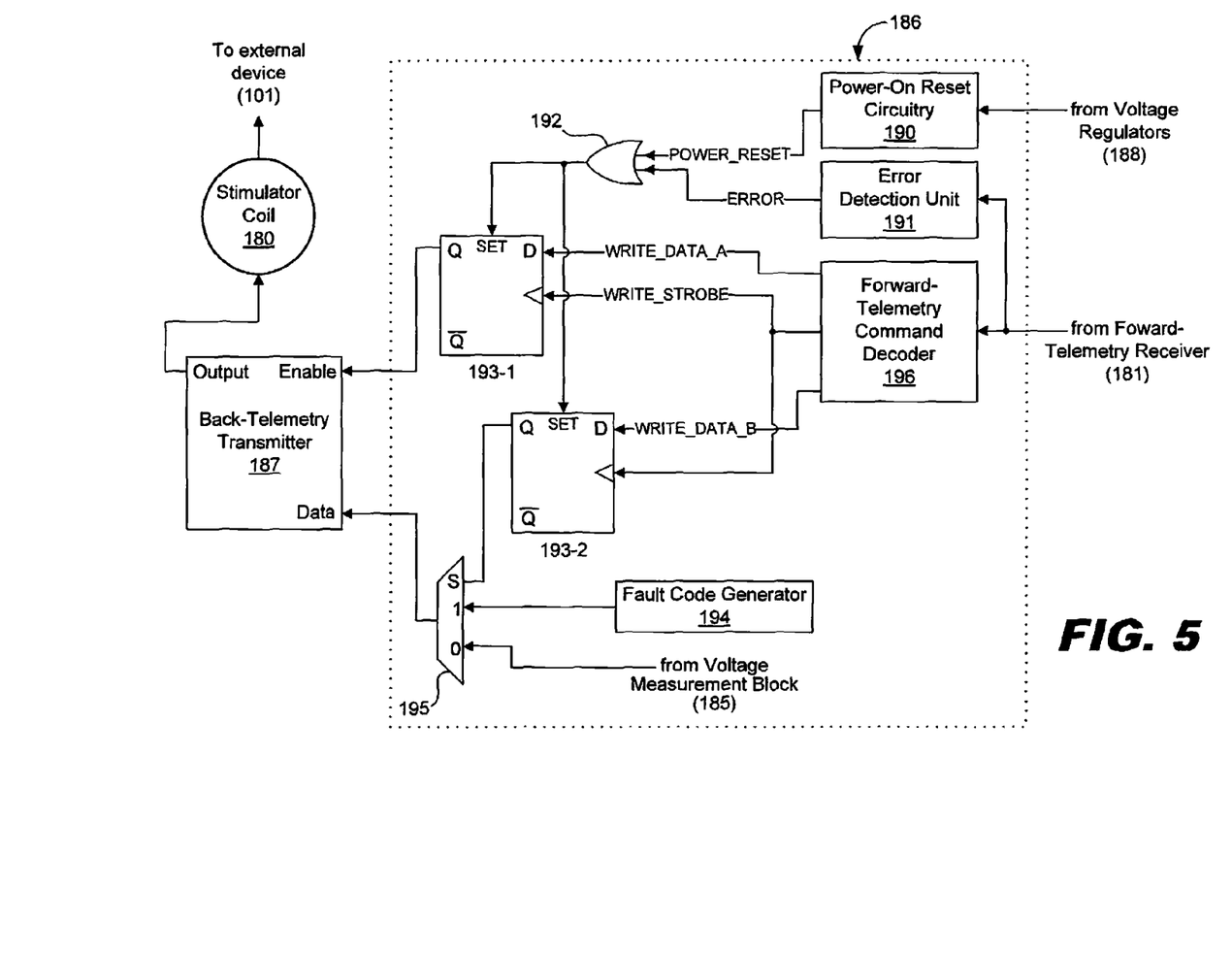
FIG. 5 is a detailed functional block diagram of a status generator and back-telemetry transmitter according to principles described herein.

FIG. 5 is a more detailed functional block diagram of the status generator 186 and back-telemetry transmitter 187. It will be recognized that the status generator 186 and back-telemetry transmitter 187 may be configured to perform additional or alternative functions as best serves a particular application. Moreover, it will be recognized that each of the functional blocks shown in FIG. 5 may include any combination of hardware, software, and/or firmware as best serves a particular application.

As shown in FIG. 5, the status generator 186 may include power-on reset circuitry 190 configured to monitor power voltages in the stimulator 100 and generate a POWER_RESET signal when supply voltages are below acceptable operating limits. The POWER_RESET signal may include any type of signal as best serves a particular application.

An error detection unit 191 may also be included within the status generator 186. The error detection unit 191 is configured to monitor the forward-telemetry data stream and check patterns within the data stream that would indicate either errors in the forward-telemetry link 103 or in the data (e.g., stimulation parameters) sent over the forward-telemetry link 103. If an error is detected, the error detection unit 191 may be configured to generate an ERROR signal.

As shown in FIG. 5, the POWER_RESET and ERROR signals may be combined by an OR gate 192. The output of the OR gate 192 may then be input into a one or more control state flip-flops 193-1 and 193-2, referred to collectively as 193. The flip-flops 193 may include any type of flip-flop. In some examples, as shown in FIG. 5, the flip-flops 193 include D flip-flops.

The flip-flops 193, when set, enable or "turn on" the back-telemetry transmitter 187. Furthermore, the flip-flops 193, when set, select a fault code generated by a fault code generator 194 as the data that is transmitted by the back-telemetry transmitter 187 to the external device 101. In some examples, the fault code is included within a fault signal that is transmitted by the back-telemetry transmitter 187 to the external device 101. The fault code may include sequence of data recognizable by the external device 101 and may be used to indicate any type of error and/or malfunction of the stimulator 100.

In some examples, the fault code is transmitted to the external device 101 during a power-up or start-up procedure. In this manner, the external device 101 may be configured to recognize the fault code at a later point in time.

In some examples, the fault code may be multiplexed with one or more voltage measurements obtained by the voltage measurement block 195. To this end, one or more data multiplexers 195 may be included within the status generator 186. The voltage measurements may be used by the external device 101 to determine optimal stimulation parameters, assess stimulator functionality, or for any other purpose as best serves a particular application.

Hence, one or more of the components shown in FIG. 5 are configured to allow the stimulator 100 to automatically enable the back-telemetry transmitter 187 and send one or more fault status signals to the external device 101 when an error, malfunction, and/or power reset occurs within the stimulator 100. In some examples, the stimulator 100 may automatically enable the back-telemetry transmitter 187 and transmit one or more status signals at any time, even while the stimulator 100 is being powered up after being turned off. Moreover, the stimulator 100 may additionally be configured to automatically cease stimulation if an error or malfunction is detected.

As shown in FIG. 5, a forward-telemetry command decoder 196 may additionally or alternatively be included within the status generator 186. The decoder 196 is configured to decode one or more commands transmitted by the external device 101 to the stimulator 100. For example, the external device 101 may transmit a command to the stimulator 100 to specifically enable or turn on the back-telemetry transmitter 187. The command decoder 196 may decode this command and enable the back-telemetry transmitter 187 accordingly.

Additionally or alternatively, the external device 101 may disable the back-telemetry transmitter 187 by transmitting one or more commands that are decoded by the command decoder 196. For example, the external device 101 may disable the back-telemetry transmitter 187 after processing a fault status signal and performing corrective action related to the fault status signal. In addition, the external device 101 may select alternative sources of data to be transmitted via the back-telemetry transmitter 187 by sending corresponding commands to the command decoder 196.

Figure 6:
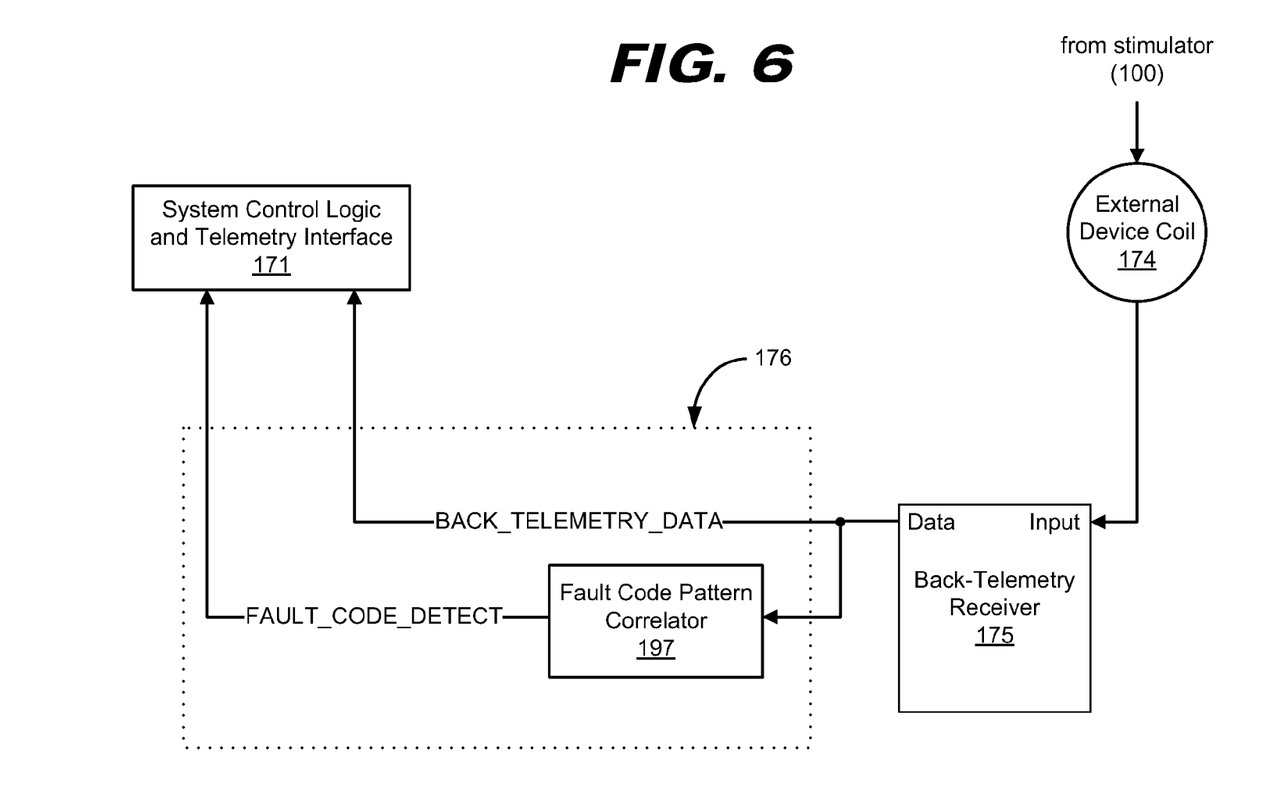
FIG. 6 is a detailed functional block diagram of a back-telemetry receiver and status detector located within the external device according to principles described herein.

FIG. 6 is a more detailed functional block diagram of the back-telemetry receiver 175 and status detector 176 located within the external device 101. It will be recognized that the back-telemetry receiver 175 and status detector 176 may be configured to perform additional or alternative functions as best serves a particular application. Moreover, it will be recognized that each of the functional blocks shown in FIG. 6 may include any combination of hardware, software, and/or firmware as best serves a particular application.

As shown in FIG. 6, the back-telemetry receiver 175 is configured to receive a signal from the implanted stimulator 100 via the coil 174 located within the external device 101. The signal may include, but is not limited to, one or more status signals generated by the status generator 186 within the stimulator 100. In some examples, the back-telemetry receiver 175 is configured to extract a digital data stream from the signal transmitted from the stimulator 100. The extracted data stream is labeled BACK_TELEMETRY_DATA in FIG. 6 for illustrative purposes.

The extracted data stream may be input into the system control logic and telemetry interface 171, as shown in FIG. 6. Additionally or alternatively, the extracted data stream may be input into the status detector 176. In some examples, the status detector 176 includes a fault code pattern correlator 197. The correlator 197 may be configured to compare the extracted data with one or more known fault code patterns. If a match is found, the correlator 197 generates a FAULT_CODE_DETECT signal to indicate that a fault has been detected in the implanted stimulator 100. The FAULT_CODE_DETECT signal is also input into the system control logic and telemetry interface 171 to signal to the external device 101 that a fault has been detected in the implanted stimulator 100.

Hence, the components described in connection with FIGS. 4-6 allow the implantable stimulator 100 to automatically enable the back-telemetry transmitter 187 and transmit a known, recognizable fault code following power-up and whenever an error occurs. The external device 101 is configured to detect the fault code pattern and reboot the stimulator 100 or otherwise remedy the error.

Figure 7:
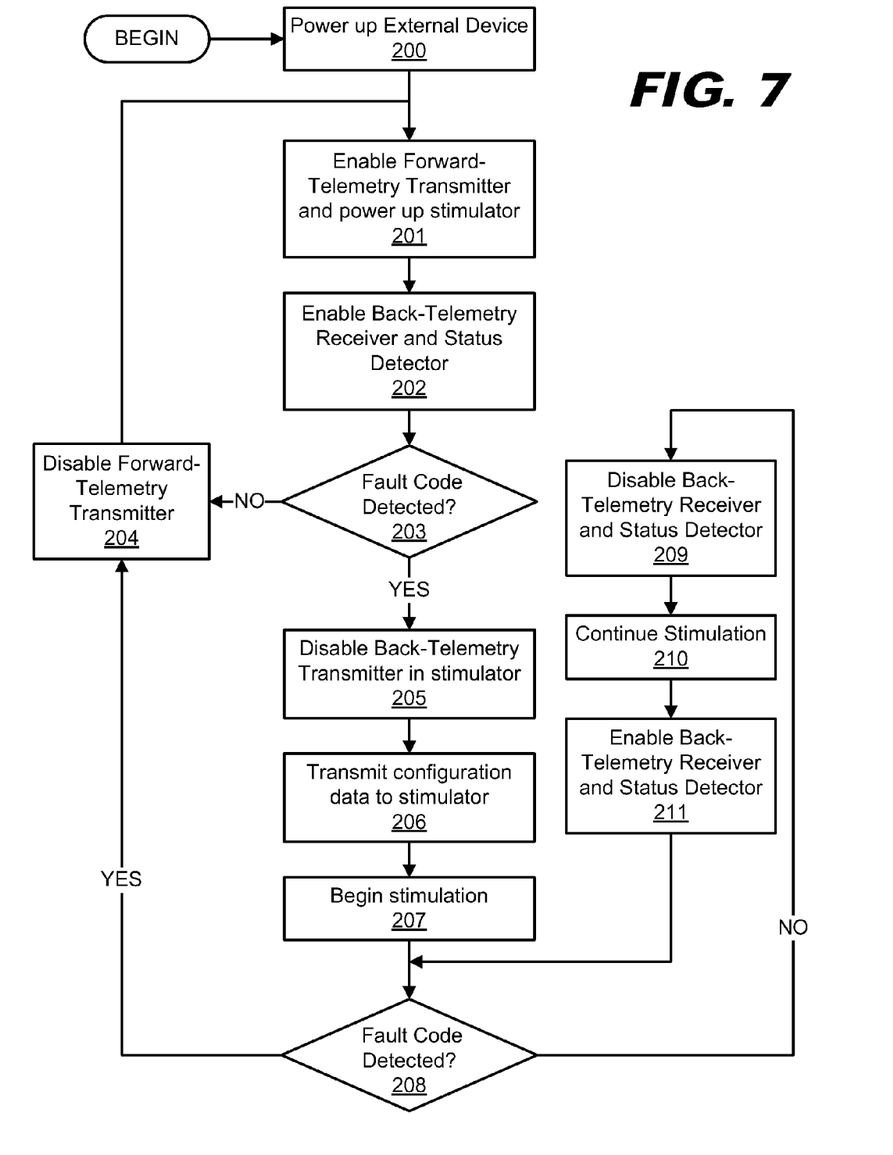
FIG. 7 is a flow chart illustrating an exemplary method of monitoring the status of an implanted stimulator according to principles described herein.

FIG. 7 is a flow chart illustrating an exemplary method of monitoring the status of an implanted stimulator 100. The steps shown in FIG. 7 are merely exemplary and may be modified, reordered, and/or added to as best serves a particular application. In some examples, one or more of the steps included within the flow chart of FIG. 7 are controlled and/or coordinated by the system control logic and telemetry interface 171 included within the external device 101. However, it will be recognized that any other component within the external device 101 and/or the stimulator 100 may additionally or alternatively be configured to control and/or coordinate one or more of the steps shown in FIG. 7.

As shown in FIG. 7, the external device 101 is first powered up (step 200). The external device 101 then enables its forward-telemetry transmitter 173 and powers up the stimulator 100 (step 201). As used herein, with reference to the components and/or devices shown in FIGS. 1-6, the term "enable" will used to refer to any action that "turns on," supplies power to, or otherwise causes a particular component and/or device to function. With the forward-telemetry transmitter 173 enabled, the external device 101 may supply power to the implantable stimulator 100 via the forward-telemetry link 103.

After a period of time, the external device 101 enables its back-telemetry receiver 175 and status detector 176. It will be understood that if the stimulator 100 has powered up correctly, its back-telemetry transmitter 187 may be configured to automatically transmit a fault code. The back-telemetry receiver 175 and status detector 176 may then attempt to detect the fault code transmitted by the stimulator 100 in order to verify a successful power up of the stimulator 100 (step 203).

If the fault code is not detected (No; step 203), the status detector 176 indicates that the stimulator 100 has not powered up as expected. Such a failure in power-up of the stimulator 100 may be caused by the coils 174, 175 being misaligned and/or being too far away from each other. The failure in power-up may additionally or alternatively be caused by any other device malfunction or error.

Once it has been determined that the stimulator 100 has not powered up correctly, the external device 101 may then temporarily disable its forward-telemetry transmitter 173 (step 204). In this manner, the stimulator 100 is powered down. Steps 201-204 are then repeated in an attempt to reboot the stimulator 100 and elicit the fault code from the stimulator 100.

If the fault code is detected (Yes; step 203), the external device 101 recognizes that the stimulator 100 has powered up correctly. The back-telemetry transmitter 187 within the stimulator 100 is then disabled (step 205) to conserve power. In some examples, the external device 101 is configured to disable the back-telemetry transmitter 187 by sending a command via the forward-telemetry link 103 as described previously. Additionally or alternatively, the stimulator 100 may be configured to automatically disable the back-telemetry transmitter 187 once the fault code has been detected. The back-telemetry transmitter 187 may alternatively be manually disabled by a clinician or by the patient.

The external device 101 may then transmit configuration data, one or more stimulation parameters, and/or other control data to the stimulator 100 via the forward-telemetry link 103 (step 206). The stimulator 100 may then begin stimulation (step 207). It will be recognized that the external device 101 may be configured to periodically or continuously transmit data including, but not limited to, one or more stimulation parameters to the stimulator 100 while the stimulator 100 is operating.

If the stimulator 100 detects an error, it may be configured to automatically enable the back-telemetry transmitter 187 and transmit a fault code via the back-telemetry link 104 to the external device 101. The error may include an error in one or more voltage levels, an error in the forward-telemetry data, a power reset of the stimulator 100, or any other error or malfunction of the stimulator 100. In some examples, the stimulator 100 may additionally be configured to cease stimulation when an error is detected. In some examples, the external device 101 may be configured to specify the types of errors that result in the fault code being generated. Moreover, different fault codes corresponding to different types of errors may be generated and transmitted by the stimulator 100.

During the course of stimulation, the external device 101 periodically enables its back-telemetry receiver 175 and status detector 176 and attempts to detect a fault code. In some alternative embodiments, only the back-telemetry receiver 175 is initially enabled. If a fault code is detected, the external device 101 enables the status detector 176 in order to process the fault code.

Hence, as shown in step 208, if a fault code is not detected (No; step 208), the back-telemetry receiver 175 and status detector 176 are disabled to conserve power. Alternatively, the back-telemetry receiver 175 and status detector 176 may remain constantly enabled. Stimulation continues for a period of time (step 210) after which the external device 101 again enables its back-telemetry receiver 175 and status detector 176 and attempts to detect a fault code. Steps 208-211 are repeated until a fault code is detected (Yes; step 208), indicating that an error has occurred within the stimulator 100. The forward-telemetry transmitter 204 within the external device 101 may then be disabled (step 204) and the stimulator 100 rebooted. Alternatively, the external device 101 may remedy the error by, for example, sending one or more corrective signals to the stimulator 100. If a fault code is never detected, steps 208-211 are repeated indefinitely until a user turns off the external device 101 or until the power supply is diminished.

As mentioned, the external device 101 may be configured to specifically enable or turn on the back-telemetry transmitter 187. In some examples, the back-telemetry transmitter 187 may be enabled to perform diagnostic functions such as status register reading, measurement of stimulator supply voltages, measurement of electrode impedance, and neural response imaging (NRI).

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method, comprising: powering up a device implanted within a patient with an external device; transmitting a fault signal with a back-telemetry signal within said implanted device to said external device in response to being powered up by said external device, wherein the fault signal is for the external device to verify a successful power up of the implanted device; disabling said back-telemetry transmitter within said implanted device after said implanted device is powered up; detecting an error with said implanted device; generating an additional fault signal corresponding to said error with said implanted device; turning on said back-telemetry transmitter after said fault signal has been generated; and transmitting said additional fault signal to said external device with said back-telemetry transmitter.

2. The method of claim 1, further comprising using said additional fault signal to remedy said error.

3. The method of claim 1, wherein said error comprises at least one or more of an error in one or more voltage levels, an error in data transmitted from the external device, a power reset of said implantable device, and a malfunction of one or more components within said implantable device.

4. A method comprising: powering up a device implanted within a patient with an external device; transmitting, by the implanted device, a fault signal with a back-telemetry transmitter to the external device in response to being powered up by the external device, wherein the fault signal is for the external device to verify a successful power up of the implanted device; verifying, by the external device, a functionality of the implanted device by detecting the fault signal; disabling, by the external device, the back-telemetry transmitter of the implanted device after the functionality of the implanted device is verified; detecting, by the implanted device, an error associated with the implanted device while the back-telemetry transmitter is disabled; generating, by the implanted device, another fault signal when the error is detected; enabling, by the implanted device, the disabled back-telemetry transmitter when the error is detected; and transmitting, by the implanted device, the another fault signal with the enabled back-telemetry transmitter to the external device; and disabling, by the implanted device, the back-telemetry transmitter after the another fault signal is received by the external device.

5. The method of claim 4, further comprising:
    detecting, by the external device, one or more fault codes contained within the another fault signal; and
    using, by the external device, the one or more fault codes to remedy the error.

6. The method of claim 5, further comprising remedying, by the external device, the error by rebooting the implanted device.

7. The method of claim 4, further comprising periodically turning on, by the external device, a receiver of the external device to detect a presence of the another fault signal.

8. The method of claim 4, wherein the error comprises at least one or more of an error in one or more voltage levels, an error in data transmitted from the external device, a power reset of the implanted device, and a malfunction of one or more components within the implanted device.

9. The method of claim 4, wherein the implanted device comprises an implantable stimulator.

10. The method of claim 9, further comprising automatically ceasing, by the implantable stimulator, stimulation when the error is detected.

11. The method of claim 4, wherein the implanted device comprises an implantable cochlear stimulator and wherein the external device comprises a speech processor.

12. A method comprising: transmitting, by a back-telemetry transmitter included in a device implanted within a patient, a fault signal to an external device via a back-telemetry link, wherein the fault signal is transmitted when the external device powers up the implanted device and is for the external device to verify a successful power up of the implanted device; disabling, by a status generator included in the implanted device, the back-telemetry transmitter after the fault signal is transmitted to the external device; detecting, by the status generator, an error associated with the implanted device while the back-telemetry transmitter is disabled; generating, by the status generator, another fault signal when the error is detected; enabling, by the status generator, the disabled back-telemetry transmitter when the error is detected; causing, by the status generator, the enabled back-telemetry transmitter to transmit the another fault signal to the external device; and disabling, by the status generator, the back-telemetry transmitter after the another fault signal is received by the external device.

13. The method of claim 12, further comprising receiving, by a forward-telemetry receiver included in the implanted device, one or more signals configured to remedy the error from the external device.

14. The method of claim 13, wherein the one or more signals are configured to remedy the error by rebooting the implanted device.

15. The method of claim 12, wherein the error comprises at least one or more of an error in one or more voltage levels, an error in data transmitted from the external device, a power reset of the implanted device, and a malfunction of one or more components within the implanted device.

* * * * *